US007007396B2

(12) United States Patent
Rudko et al.

(10) Patent No.: US 7,007,396 B2
(45) Date of Patent: Mar. 7, 2006

(54) REPLACEMENT HEART VALVE SIZING DEVICE

(75) Inventors: Robert I. Rudko, Holliston, MA (US); Richard P. Yeomans, Jr., Medway, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 0 days.

(21) Appl. No.: 10/447,532

(22) Filed: May 29, 2003

(65) Prior Publication Data

US 2004/0237321 A1    Dec. 2, 2004

(51) Int. Cl.
*A61B 1/005*    (2006.01)
(52) U.S. Cl. .............................. 33/512; 33/542; 600/587
(58) Field of Classification Search ............... 33/512, 33/558.01, 558.03, 558.04, 542, 544, 544.2, 33/555.1, 558.2, 558.4, 455, 543; 600/587, 600/591, 593; 606/191, 198, 102; 604/104; 623/2.11
See application file for complete search history.

(56) References Cited

U.S. PATENT DOCUMENTS

| | | | | |
|---|---|---|---|---|
| 467,852 A | * | 1/1892 | Buckelew | 33/558.01 |
| 1,858,544 A | * | 5/1932 | Erickson | 33/544 |
| 2,267,110 A | * | 12/1941 | Kinley et al. | 33/544.2 |
| 3,271,869 A | * | 9/1966 | Ratner | 33/558.03 |
| 3,505,987 A | * | 4/1970 | Heilman | 600/18 |
| 3,533,166 A | * | 10/1970 | Pino, Jr. | 33/544 |
| 3,555,689 A | * | 1/1971 | Cubberly, Jr. | 33/544.3 |
| 3,772,794 A | * | 11/1973 | Hopler, Jr. | 33/544.2 |
| 4,213,246 A | * | 7/1980 | Stevens | 33/544 |
| 4,407,157 A | * | 10/1983 | Lichtenberg | 73/152.17 |
| 4,411,648 A | * | 10/1983 | Davis et al. | 604/21 |
| 4,587,975 A | * | 5/1986 | Salo et al. | 600/506 |
| 5,074,871 A | * | 12/1991 | Groshong | 606/170 |
| 5,171,248 A | * | 12/1992 | Ellis | 606/102 |
| 5,176,693 A | * | 1/1993 | Pannek, Jr. | 606/159 |
| 5,238,005 A | * | 8/1993 | Imran | 600/585 |
| 5,275,169 A | * | 1/1994 | Afromowitz et al. | 600/486 |
| 5,356,382 A | * | 10/1994 | Picha et al. | 604/105 |
| 5,370,685 A | | 12/1994 | Stevens | |
| 5,398,691 A | * | 3/1995 | Martin et al. | 600/463 |
| 5,411,552 A | | 5/1995 | Andersen et al. | |
| 5,428,903 A | * | 7/1995 | Pocci | 33/558.01 |
| 5,465,732 A | * | 11/1995 | Abele | 600/585 |
| 5,499,995 A | * | 3/1996 | Teirstein | 606/192 |
| 5,545,214 A | | 8/1996 | Stevens | |
| 5,554,185 A | | 9/1996 | Block et al. | |
| 5,562,665 A | * | 10/1996 | Young | 606/62 |
| 5,607,462 A | * | 3/1997 | Imran | 607/122 |

(Continued)

OTHER PUBLICATIONS

U.S. Appl. No. 10/753,693, filed Jul. 7, 2004, Rudko et al.

(Continued)

*Primary Examiner*—Christopher W. Fulton
*Assistant Examiner*—Amy R. Cohen
(74) *Attorney, Agent, or Firm*—Iandiorio & Teska

(57) ABSTRACT

A heart valve sizing system featuring a lumen advanceable in vasculature, an inside caliper device at the distal end of the lumen, and a readout for reading the dimension gauged by the inside caliper device. In the preferred embodiment, the inside caliper device includes a four bar linkage with first and second opposing pivot points and third and fourth opposing pivot points and a push rod connected to the second pivot point for alternatively urging the third and fourth pivot points together when extended and urging the third and fourth pivot points apart when retracted to gauge the inside dimension of the vasculature.

15 Claims, 5 Drawing Sheets

U.S. PATENT DOCUMENTS

| | | | |
|---|---|---|---|
| 5,728,123 A * | 3/1998 | Lemelson et al. | 604/22 |
| 5,830,210 A * | 11/1998 | Rudko et al. | 606/15 |
| 5,840,081 A | 11/1998 | Andersen et al. | |
| 5,885,244 A * | 3/1999 | Leone et al. | 604/508 |
| 5,899,915 A * | 5/1999 | Saadat | 606/170 |
| 6,010,511 A * | 1/2000 | Murphy | 606/108 |
| 6,033,359 A * | 3/2000 | Doi | 600/117 |
| 6,081,737 A * | 6/2000 | Shah | 600/393 |
| 6,106,515 A | 8/2000 | Winston et al. | |
| 6,110,200 A * | 8/2000 | Hinnenkamp | 623/2.11 |
| 6,168,614 B1 | 1/2001 | Andersen et al. | |
| 6,287,321 B1 | 9/2001 | Jang | |
| 6,425,916 B1 | 7/2002 | Garrison et al. | |
| 6,450,976 B1 * | 9/2002 | Korotko et al. | 600/587 |
| 6,485,485 B1 | 11/2002 | Winston et al. | |
| 6,517,515 B1 * | 2/2003 | Eidenschink | 604/101.05 |
| 6,560,889 B1 * | 5/2003 | Lechen | 33/544 |
| 6,764,453 B1 * | 7/2004 | Meier | 600/587 |
| 6,908,478 B1 * | 6/2005 | Alferness et al. | 623/1.11 |
| 2002/0058995 A1 | 5/2002 | Stevens | |
| 2002/0095116 A1 | 7/2002 | Strecter | |

OTHER PUBLICATIONS

U.S. Appl. No. 10/628,794, filed Jul. 28, 2003, Rudko et al.
U.S. Appl. No. 10/600,175, filed Jun. 20, 2003, Rudko et al.

* cited by examiner

REPLACEMENT HEART VALVE SIZING DEVICE

FIELD OF THE INVENTION

This invention relates to aortic valve replacement.

BACKGROUND OF THE INVENTION

Currently, replacement of a malfunctioning heart valve is accomplished by a major open-heart surgical procedure requiring general anesthesia, full cardio-pulmonary bypass with complete cessation of cardio-pulmonary activity, and a long period of hospitalization and recuperation. In most cases, the native valve is resected (cut-out) and the replacement valve then installed.

The appropriate size replacement valve is determined using plugs. The surgeon chooses a plug from a tray of plugs increasing in size by 1 mm increments or so. If the chosen plug is too loose in the patient's aorta, a larger plug is chosen; if the plug chosen is to large to fit in the patient's aorta, a smaller plug is chosen, and so on until the chosen plug fits just right. Then, a replacement valve of a size corresponding to the size of the correct plug is installed and stitched in place. As can probably be ascertained, the use of plugs to correctly size the replacement valve results in a time consuming and somewhat inexact procedure.

As an alternative to open heart surgery, those skilled in the art have attempted to devise systems for endovascular heart valve replacement to overcome the disadvantages associated with open-heart surgery. U.S. Pat. No. 5,370,685, for example, discloses a procedure device capsule connected to a tube and delivered to the site via a guide wire introduced in the femoral artery of a patient. The device capsule houses an expandable barrier attached to balloon segments. Once the guide wire is removed and the barrier is expanded, a tissue cutting blade assembly is advanced in the tube and rotated by a DC motor to resect the existing valve. The barrier traps any debris cut by the tissue cutting blade assembly. Tissue is then suctioned out via the tube. Next, the cutting blade assembly is removed, the barrier balloons are deflated, and the barrier is brought back into the capsule and the capsule itself is removed.

Then, a valve introducer capsule is advanced to the situs. The capsule houses a replacement valve and includes a pusher disk and inflatable balloon segments. After the balloon segments are inflated, the pusher disk pushes the replacement valve into position and a mounting balloon is used to expand the replacement valve and to secure it in place. Then, the introducer capsule is removed. The '685 patent is hereby incorporated herein. See also U.S. Pat. Nos. 5,545,214; 6,168,614; 5,840,081; 5,411,552; 5,370,685; and published U.S. Patent Application No. 2002/0058995 A1. These patents are also incorporated herein.

Other relevant art includes the following, also included herein by this reference. Published U.S. Patent Application No. 2002/0095116 A1 discloses an aortic filter, an artery filter, and a check valve attached to the distal end of a canula for resecting an aortic valve from within the aorta. U.S. Pat. No. 6,287,321 also discloses a percutaneous filtration catheter. U.S. Pat. No. 5,554,185 discloses an inflatable prosthetic cardiovascular valve. U.S. Pat. No. 6,425,916 discloses a percutaneous approach with a valve displacer for displacing and holding the native valve leaflets open while a replacement valve is expanded inside the native valve. In this way, the native valve does not need to be resected.

One problem with the percutaneous approach, however, is that conventional plugs can no longer be used to correctly size the replacement valve. And, the art discussed above fails to teach or suggest any alternative sizing mechanism.

BRIEF SUMMARY OF THE INVENTION

It is therefore an object of this invention to provide a percutaneous heart valve sizing mechanism which is advanceable with the vasculature of a patent for percutaneous valve replacement to facilitate choosing a replacement valve of the correct size for the patient.

It is a further object of this invention to provide a heart valve sizing mechanism which can also be used in connection with open heart surgery techniques.

It is a further object of this invention to provide a heart valve sizing mechanism which is easier and faster to use and also more exact.

The invention results from the realization that a sizing device which can be used in connection with percutaneous procedures is effected by a lumen advanceable in the patient's vasculature, an inside caliper device at the distal end of the lumen, and a mechanism for reading the dimension gauged by the caliper device.

This invention features a heart valve sizing system comprising a lumen advanceable in vasculature, an inside caliper device at the distal end of the lumen, and means for reading the dimension gauged by the inside caliper device.

In one specific embodiment, the inside caliper device includes a four bar linkage with first and second opposing pivot points and third and fourth opposing pivot points, and a push rod connected to the second pivot point for alternatively urging the third and fourth pivot points together when extended and urging the third and fourth pivot points apart when retracted to gauge the inside dimension of the vasculature. In that embodiment, the means for reading the dimension gauged by the caliper device may include a member connected on one end to the push rod, a mechanism at the other end of the member which advances and retracts the member, a position sensor which senses the position of the member, and a readout device responsive to the position sensor which correlates the position of the member to the dimension gauged by the four bar linkage.

In one example, the position sensor is a potentiometer, the readout device is a digital readout, and the member is a cable located inside the lumen. The push rod is typically retractable into the lumen and the four bar linkage may also be retractable into the lumen. Typically, the lumen is attached to a handle including the mechanism, the position sensor, and the readout device. In one embodiment, the mechanism is a turning knob threaded into the handle and connected to the member.

In one embodiment, the heart valve sizing system of this invention includes a lumen advanceable in vasculature, an inside caliper device at the distal end of the lumen, a member connected to the inside caliper device advanceable and retractable within the lumen, a position sensor which senses the position of the member, and a readout device responsive to the position sensor which correlates the position of the member to the dimension gauged by the inside caliper device. Typically, the inside caliper device includes a four bar linkage with first and second opposing pivot points and third and fourth opposing pivot points, and a push rod connected to the second pivot point for alternatively urging the third and fourth pivot points together when extended and urging the third and fourth pivot points apart when retracted to gauge the inside dimension of the vasculature.

One heart valve sizing system in accordance with this invention features a catheter advanceable in vasculature, a handle at the proximal end of the catheter, an inside caliper device at the distal end of the catheter, means for extending the inside caliper device to gauge the inside dimension of the vasculature and for retracting the inside caliper device to advance the inside caliper device in the vasculature, and means, at the handle, for detecting the extent of extension of the inside caliper device to measure the inside dimension of the vasculature.

In one example, the means for extending and retracting includes a push rod connected to one pivot point of a four bar linkage, a member connected on one end to the push rod and extending to the handle, and a knob connected to the member.

In one example, the means for detecting includes a sensor in the handle configured to sense the position of the member and a readout on the handle responsive to the sensor.

This invention also features a method of percutaneously sizing a heart valve, the method comprising: advancing a lumen with a distal inside caliper device within vasculature to the site of a valve; activating the inside caliper device to gauge the dimension measured by the inside caliper device; and reading the dimension gauged by the inside caliper device. Typically, the inside caliper device is advanced within the vasculature in a collapsed state and activating the inside caliper device includes extending the inside caliper device.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Figure 1:
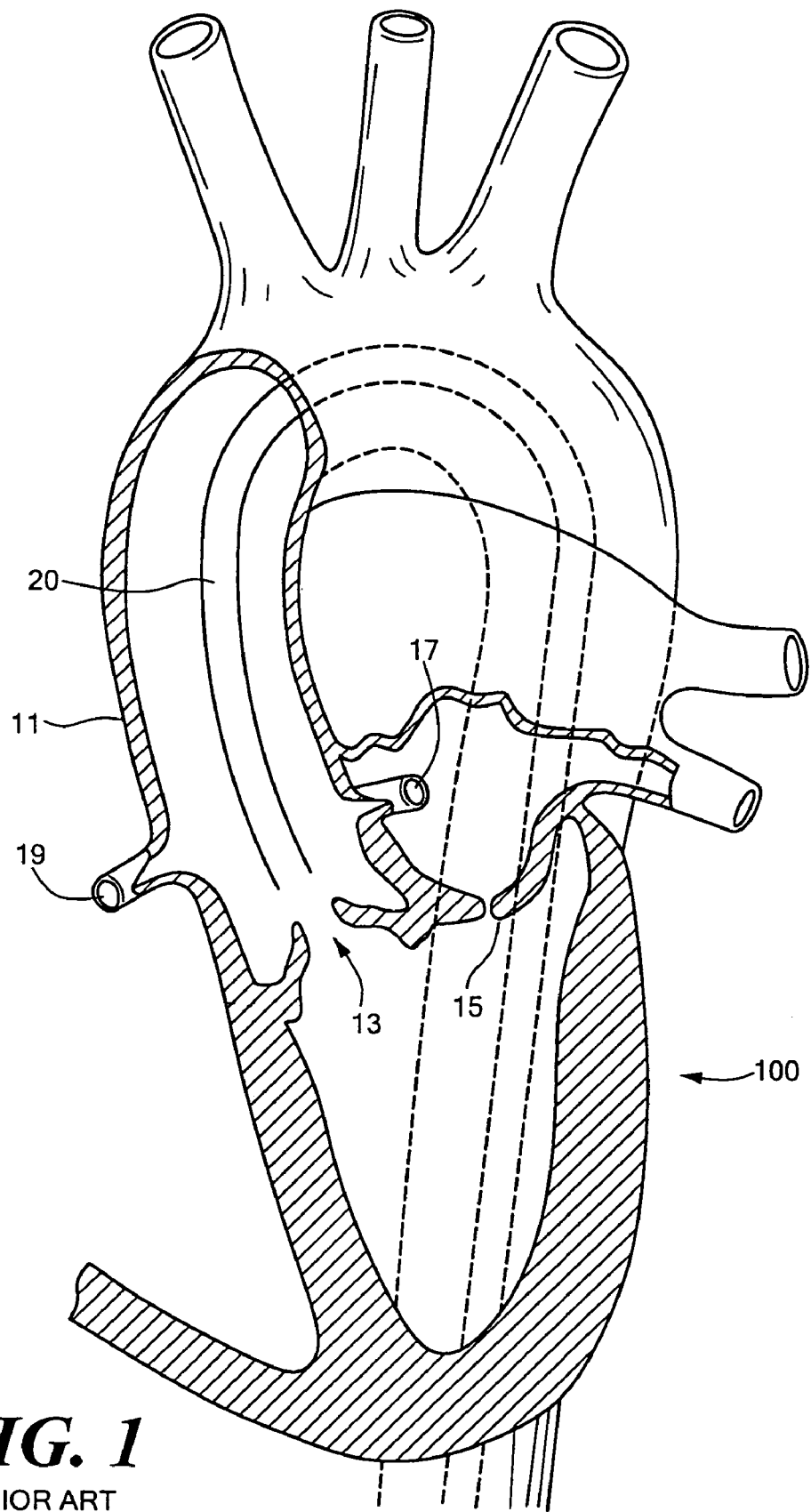
FIG. 1 is a schematic view showing a typical human heart.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

FIG. 1 schematically shows heart 100 with aorta 11, aortic valve 13, mitral valve 15, and coronary arteries 17 and 19. The idea behind percutaneous valve replacement surgery is to deliver a catheter 20 proximate valve 13 to resect it and to secure a replacement prosthetic valve in place. Resecting the native valve, however, is problematic. Those skilled in the art have devised inflatable barriers such as barrier 30, FIG. 2 used to trap tissue during resection. See also U.S. Pat. No. 6,287,321 and Published U.S. Patent Application No U.S. 2002/0095116 A1. Barrier 30 traps any tissue cut during valve resection. Tissue cutter 40, FIG. 3 with blades 42 is used to resect the native valve. Tissue cutter 40 is connected to shaft 44 rotated by a DC motor presumably at a very high rate of rotation in order to effect tissue cutting. Currently, there is no known way to percutaneously determine the size of the replacement valve.

Figure 4:
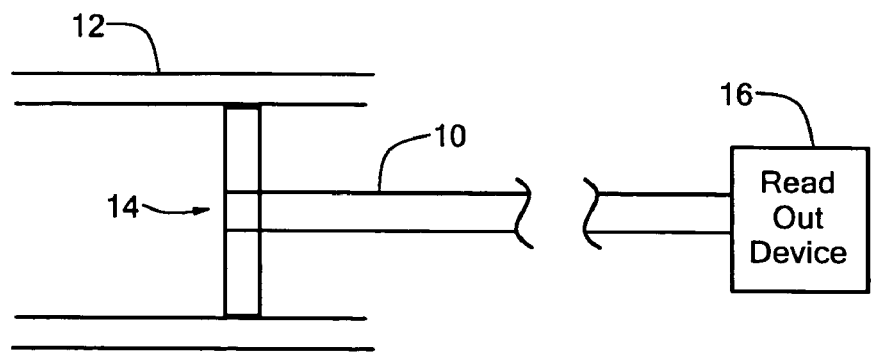
FIG. 4 is a schematic conceptual depiction of a heart valve sizing system in accordance with the subject invention.

FIG. 4 schematically depicts the heart valve sizing system of the invention. A lumen such as catheter 10 is advanceable in vasculature 12. Inside caliper device 14 is at the distal end of catheter 10 and there are means 16 for reading the dimension gauged by caliper device 14.

Figure 5:
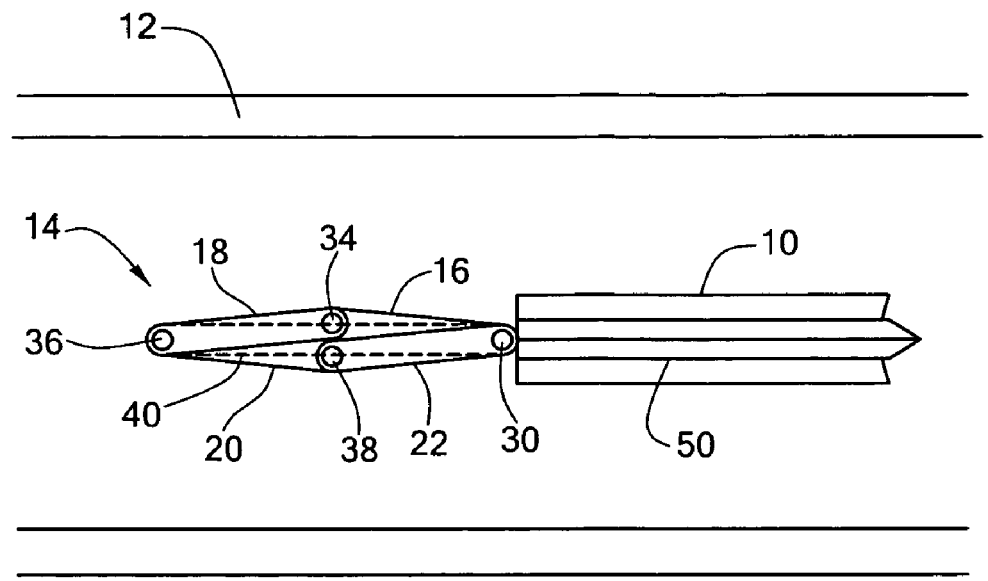
FIGS. 5 and 5A are schematic views showing one preferred embodiment of the inside caliper device of the subject invention in its retracted position.
Figure 5A:
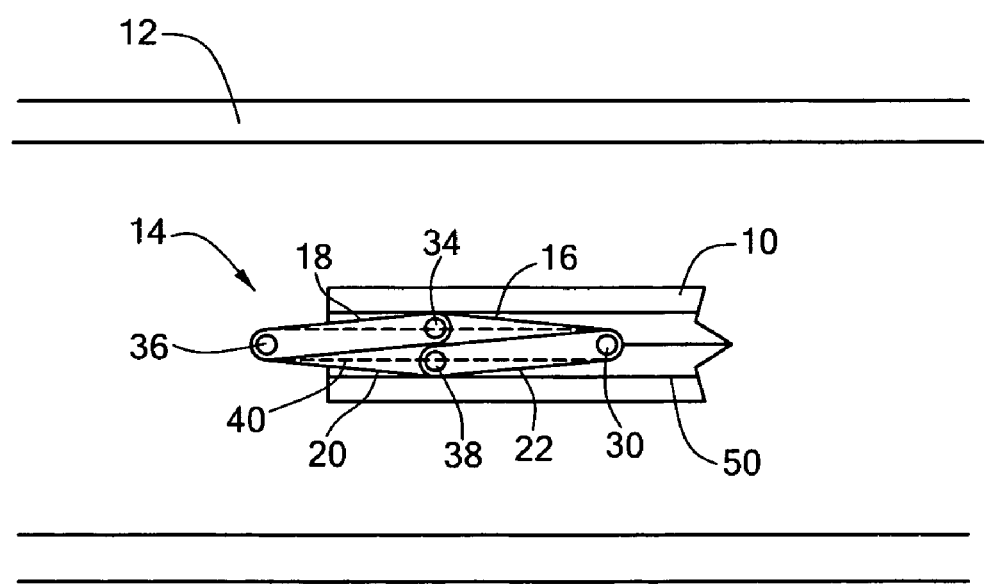
Figure 6:
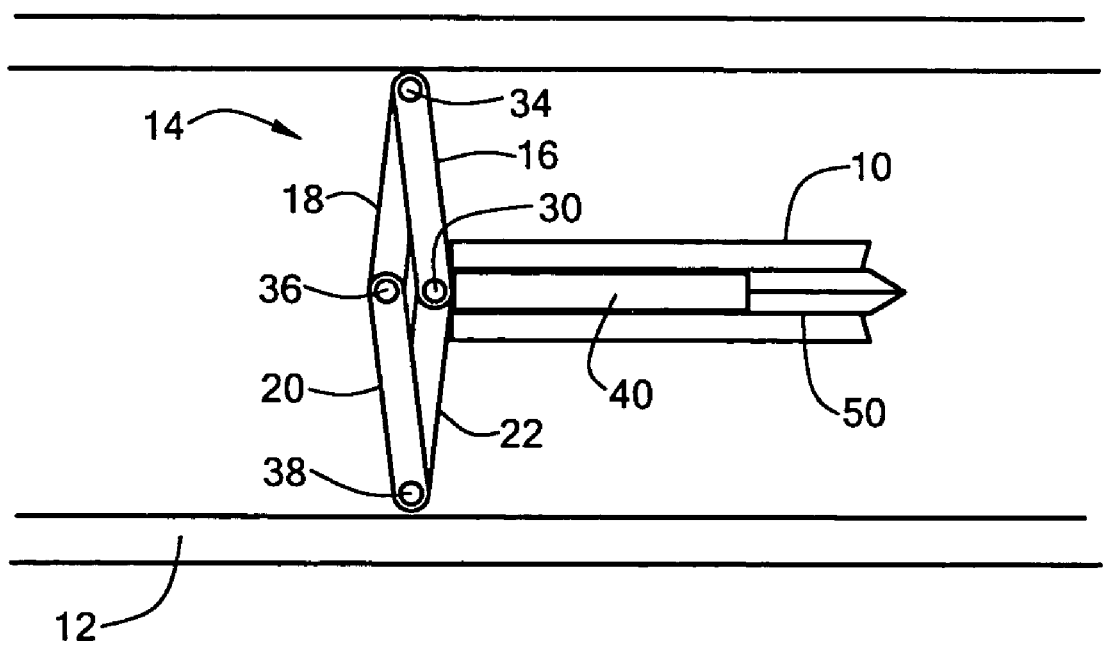
FIG. 6 is a schematic view showing the caliper device of FIG. 5 in its extended gauging position.

In the preferred embodiment, inside caliper 14, FIG. 5 includes a four bar linkage assembly with bars 16, 18, 20, and 22 pivotably connected by pins at pivot points 30, 38, 34 and 36. Pivot point 30 opposes pivot point 36 and pivot point 34 opposes pivot point 38. To extend inside caliper device 14 to gauge the inside dimension of vasculature 12 as shown in FIG. 6, push rod 40 is connected at its distal end at pivot point 36 and freely slideable with respect to pivot point 30. Thus, when push rod 40 is retracted within catheter 10 as shown in FIG. 6, pivot points 36 and 30 are urged closer together and at the same time pivot points 34 and 38 are urged further apart to gauge the inside of vasculature 12. When push rod 40 is extended as shown in FIG. 5, pivot points 34 and 38 are brought closer together and pivot points 36 and 30 urged further apart for advancement of the caliper in or withdrawal from vasculature 12. Depending upon the size and configuration of catheter 10, inside caliper device 14, FIG. 5A, may even be brought within catheter 10 itself for maneuverability. Other types of inside caliper devices may be employed, however, including three bar linkages and the like.

Figure 7:
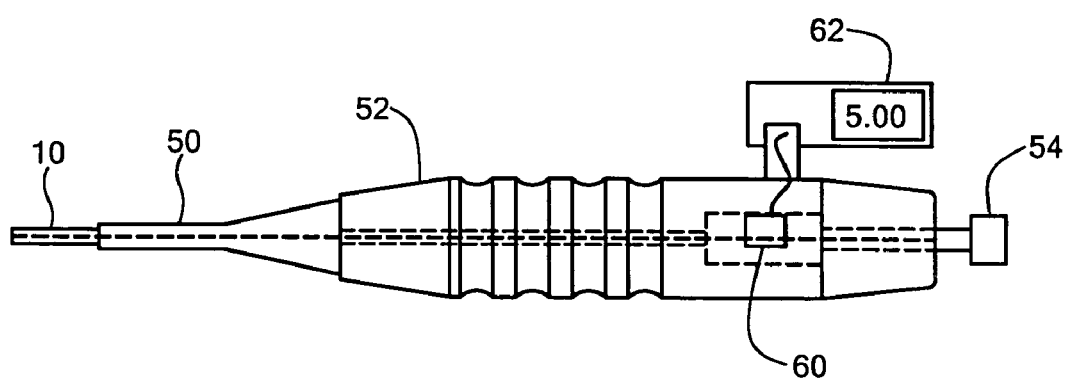
FIG. 7 is a schematic view showing the handle of the heart valve sizing system of this invention in one preferred embodiment.

Push rod 40 is driven to and fro by a member in the form of a wire or cable 50 connected to push rod 40 at one end and extending within catheter 10 to handle 52, FIG. 7 and connected to knob 54 which is threaded into handle 52 so it can advance and retract cable 10 in a precise manner. Other mechanisms for advancing and retracting and advancing the cable, however, are known in the art.

In this embodiment, the means for detecting the extent of extension of inside caliper device 14, FIGS. 5 and 6, to measure the inside dimension of vasculature 12 includes position sensor 60, FIG. 7 in handle 52 which preferably correlates the position of cable 50 to the dimension gauged by the four bar linkage and also digital readout 62 on handle 52 responsive to sensor 60. Sensor 60 is configured to optically or resistively sense the position of cable 50 and readout 62 is responsive to sensor 60. In one embodiment, sensor 60 is a sliding potentiometer and readout 62 is a liquid crystal display. When pivot points 34 and 38 contact the wall of vasculature 12, the physician will feel resistance at knob 54. Also, contacts can be added to pivot points 34 and 38 and used to electronically detect when pivot points 34 and 38 contact vasculature 12.

Other means for measuring the relative position of cable 50 within handle 52, however, are possible and in accordance with the subject invention including a rather simple system wherein the end of the cable is manually driven to and fro and the length of cable extending out of handle 52 is measured to gauge the extent of extension of inside caliper device 14, FIG. 6. Also, measurements may be taken at several locations and then averaged.

Figure 3:
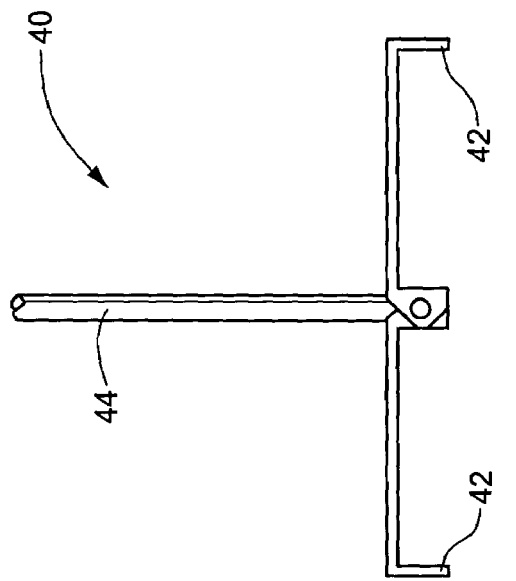
FIG. 3 is a schematic view showing a prior art tissue cutter used in endovascular aortic valve replacement procedures.
Figure 2:
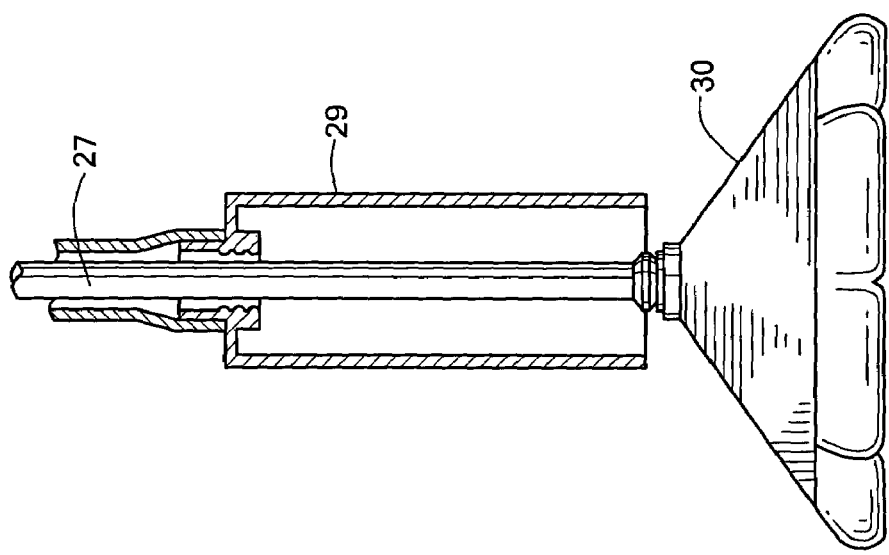
FIG. 2 is a schematic view of a prior art inflatable barrier used in endovascular aortic valve replacement procedures.

In any embodiment, the sizing system of the subject invention may be used in conjunction with the valve resection system of FIGS. 2–3 for percutaneous procedures and/or in connection with open heart procedures as well. The result is a heart valve sizing system which facilitates choosing a replacement valve of the correct size for the patient. The heart valve sizing system of the subject invention is easy to use and provides for fast vasculature sizing in an exact manner.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A heart valve sizing system comprising:
   a lumen advanceable in vasculature;
   an inside caliper device at a distal end of the lumen, the inside caliper device including:
      a four bar linkage with first and second opposing pivot points and third and fourth opposing pivot points, and
      a push rod connected to the second pivot point for alternatively urging the third and fourth pivot points together when extended and urging the third and fourth pivot points apart when retracted to gauge the inside dimension of the vasculature; and
   means for reading the dimension gauged by the inside caliper device, the means for reading including:
      a member connected on one end to the push rod,
      a mechanism at the other end of the member which advances and retracts the member,
      a position sensor which senses the position of the member, and
      a readout device responsive to the position sensor which correlates the position of the member to the dimension gauged by the four bar linkage.

2. The system of claim 1 in which the position sensor is a potentiometer.

3. The system of claim 1 in which the readout device is a digital readout.

4. The system of claim 1 in which the member is a cable located inside the lumen.

5. The system of claim 1 in which the push rod is retractable into the lumen.

6. The system of claim 1 in which the four bar linkage is retractable into the lumen.

7. The system of claim 1 in which the lumen is attached to a handle including the mechanism, the position sensor, and the readout device.

8. The system of claim 7 in which the mechanism is a turning knob threaded into the handle and connected to the member.

9. A heart valve sizing system comprising:
   a lumen advanceable in vasculature;
   an inside caliper device at a distal end of the lumen including a four bar linkage, one pivot point of the four bar linkage connected to a push rod;
   means for reading the dimension gauged by the four bar linkage when extended, the means for reading including:
      a member connected on one end to the push rod,
      a mechanism at the other end of the member which advances and retracts the member,
      a position sensor which senses the position of the member, and
      a readout device responsive to the position sensor which correlates the position of the member to the dimension gauged by the four bar linkage.

10. A heart valve sizing system comprising:
   a lumen advanceable in vasculature;
   an inside caliper device at a distal end of the lumen;
   a member connected to the inside caliper device advanceable and retractable within the lumen;
   a position sensor at a proximal end of the lumen which senses the position of the member; and
   a readout device responsive to the position sensor which correlates the position of the member to the dimension gauged by the inside caliper device.

11. The system of claim 10 in which the inside caliper device includes:
   a four bar linkage with first and second opposing pivot points and third and fourth opposing pivot points, and
   a push rod connected to the second pivot point for alternatively urging the third and fourth pivot points together when extended and urging the third and fourth pivot points apart when retracted to gauge the inside dimension of the vasculature.

12. A heart valve sizing system comprising:
   a catheter advanceable in vasculature;
   a handle at a proximal end of the catheter;
   an inside caliper device at a distal end of the catheter including a four bar linkage;
   means for extending the inside caliper device to gauge the inside dimension of the vasculature and for retracting the inside caliper device to advance the inside caliper device in the vasculature, the means for extending and retracting including a push rod connected to one pivot point of the four bar linkage and a member connected on one end to the push rod and extending to the handle; and
   means, at the handle, for detecting the extent of extension of the inside caliper device to measure the inside dimension of the vasculature, said means for detecting including a sensor in the handle configured to sense the position of the member.

13. The system of claim 12 in which the means for extending and retracting further includes a knob connected to the member.

14. The system of claim 12 in which the means for detecting further includes a readout on the handle responsive to the sensor.

15. A heart valve sizing system comprising:
   a lumen advanceable in vasculature;
   an inside caliper device at a distal end of the lumen, said inside caliper device retractable into the lumen; and
   means for reading the dimension gauged by the inside caliper device at a proximal end of the lumen, said means for reading including a member connected to the inside caliper device and a position sensor which senses the position of the member.

* * * * *